(12) United States Patent
Hickey

(10) Patent No.: US 12,329,681 B2
(45) Date of Patent: Jun. 17, 2025

(54) SURGICAL INSTRUMENTS FOR OCULAR SURGERY

(71) Applicant: Johnson & Johnson Surgical Vision, Inc., Irvine, CA (US)

(72) Inventor: Lauren M. Hickey, Los Angeles, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 778 days.

(21) Appl. No.: 17/055,595

(22) PCT Filed: Jul. 17, 2019

(86) PCT No.: PCT/IB2019/056128
§ 371 (c)(1),
(2) Date: Nov. 15, 2020

(87) PCT Pub. No.: WO2020/021397
PCT Pub. Date: Jan. 30, 2020

(65) Prior Publication Data
US 2021/0186756 A1 Jun. 24, 2021

Related U.S. Application Data

(60) Provisional application No. 62/702,775, filed on Jul. 24, 2018.

(51) Int. Cl.
*A61F 9/007* (2006.01)
(52) U.S. Cl.
CPC ................ *A61F 9/00754* (2013.01)
(58) Field of Classification Search
CPC .............. A61F 9/00754; A61F 9/00763; A61F 9/00736
See application file for complete search history.

(56) References Cited

U.S. PATENT DOCUMENTS 3,732,858 A * 5/1973 Banko .............. A61B 17/32002
606/107
3,945,375 A * 3/1976 Banko ................. A61F 9/00763
606/49

(Continued)

FOREIGN PATENT DOCUMENTS

| EP | 0458653 A1 | 11/1991 |
| EP | 1284669 B1 | 12/2006 |
| KR | 20170056618 A | 5/2017 |

OTHER PUBLICATIONS

Tabandeh, H.G.M., et. al., "Lens Hardness in Mature Cataracts," Eye, 1994, vol. 8 (Pt 4), pp. 453-455.

(Continued)

*Primary Examiner* — Anh T Dang

(57) ABSTRACT

A handpiece for ocular surgery that includes a handle having at least inlets for irrigation and aspiration; a sleeve extending distally from a first end of the handle, wherein the sleeve comprises a bore extending a length of the sleeve along a central axis of the sleeve, and includes at least one port suitable to deliver irrigation from the irrigation inlet substantially distal from the first end of the handle; the aspiration being provided between an aspiration inlet and a distal bore port; a motor coupled with a second end of the handle and having a shaft; and an auger associated with the shaft, and extending at least partially through an interior portion of the handle between the second and the first ends and extending along the length of the sleeve, wherein a tip of the auger distal to the shaft is advanced by actuation of the motor.

19 Claims, 5 Drawing Sheets

(56) References Cited

U.S. PATENT DOCUMENTS

| | | | |
|---|---|---|---|
| 5,891,153 A | 4/1999 | Peterson | |
| 6,217,543 B1 | 4/2001 | Anis et al. | |
| 6,217,584 B1 | 4/2001 | Nun | |
| 2006/0253069 A1* | 11/2006 | Li | A61B 17/32002 604/93.01 |
| 2007/0128070 A1* | 6/2007 | Wu | B01L 3/5023 422/400 |
| 2012/0078224 A1* | 3/2012 | Lerner | A61F 9/0017 604/218 |
| 2012/0172905 A1* | 7/2012 | Lee Shee | A61B 17/1671 76/115 |
| 2014/0277039 A1* | 9/2014 | Liberatore | A61B 17/32053 606/167 |
| 2016/0030061 A1* | 2/2016 | Thommen | A61B 17/32002 606/80 |
| 2017/0224888 A1 | 8/2017 | Hickey et al. | |
| 2018/0049921 A1 | 2/2018 | Sorensen et al. | |

OTHER PUBLICATIONS

Zacharias, J., "Role of Cavitation In thePhacoemulsification Process," Journal of Cataract & Refractive Surgery, May 2008, vol. 34 (5), pp. 846-852.

\* cited by examiner

SURGICAL INSTRUMENTS FOR OCULAR SURGERY

CROSS REFERENCE TO RELATED APPLICATIONS

This application is a U.S. national stage of and claims the benefit under 35 U.S.C. § 371 of International Patent Application No. PCT/IB2019/056128, filed Jul. 17, 2019, which claims the benefit under 35 U.S.C. § 119 (e) of U.S. Provisional Patent Application No. 62/702,775, filed Jul. 24, 2018, which is are incorporated herein by reference in their entirety.

FIELD OF THE DISCLOSURE

The disclosure relates to medical instruments, and more specifically, to surgical instruments for performing ocular surgery.

BACKGROUND

A cataract is a type of visual impairment, and is defined as an opacity in the crystalline lens of the eye, which interferes with vision. Once visual function has been compromised by a cataract, surgery is performed to remove the opaque lens in order to restore proper eye function. Cataracts are the most prevalent disabling eye disease worldwide.

Many methods of cataract extraction have been developed. Some of these methods require large incisions that are unstable and require prolonged recovery times. More current techniques generally require making much smaller incisions in the eye, and removing the cataract from the eye through this small incision. Smaller incisions, of course, result in more rapid post-operative recovery and a more structurally stable eye. Thus, the presently preferred surgical method of cataract extraction is extracapsular removal, such as by extracapsular surgery or phacoemulsification, through a very small incision.

More specifically, surgeries today typically involve making a very small incision (2-7 mm) in the eye, and either removing the cataractous nucleus intact or emulsifying/fragmenting the nucleus and mechanically removing the pieces through the incision. As referenced above, smaller incision sizes are preferably, although the smaller the incision the greater the fragmentation of the cataract that is required to remove it from the eye.

Yet more particularly, phacoemulsification typically utilizes ultrasonic energy to emulsify a cataract nucleus and aspirates the cataract from the eye through the aforementioned small incision. Of note, the advent of foldable intraocular lenses to complete this surgery has resulted in sutureless surgery of even the referenced small incision with virtually immediate visual and functional recovery. For these and other reasons, phacoemulsification has become the most practiced method of cataract surgery. Nevertheless, phacoemulsification is very expensive, and requires expensive and sophisticated equipment that demands significant expertise to operate safely.

Further, ultrasonic phacoemulsification can suffer impediments to optimal performance. For example, cavitation bubbles which result from ultrasonic activity in a liquid may adversely impact phacoemulsification results. Corneal burns can also occur due to the friction of the phacoemulsification tip and the eye incision, which friction results from the ultrasonic vibration of the phacoemulsification tip. That is, corneal burns may result from the maintaining of contact between the emulsifying instrument as it vibrates and the cornea. Corneal burn is the highest occurrence of adverse clinical impact to the patient in intraocular surgery.

As such, the use of a non-ultrasonic handpiece, if a small incision size could be maintained, might eliminate some known adverse impacts on surgical performance, and hence may improve ocular surgical outcomes. Moving to a non-ultrasonic handpiece may additionally simplify the required surgical console and console driver, thereby lowering the required expertise and experience to perform ocular surgery, which additionally would decrease the cost of surgery.

Some non-ultrasonic ocular surgical instruments that have been utilized in removing cataractous nucleii include screw-like distal cutting elements, which generally consist of a small bore rotating cutting element that is maintained in continuous physical contact with the cataract. However, because such methods typically lack an ability to maintain position, and lack the aspiration and irrigation elements typical in phacoemulsification, maintenance of continued contact between the cutting element and cataract becomes very difficult, and fragments of the cataract are overly free to float about inside the eye in a variably pressurized environment, thereby complicating cataract removal and increasing the likelihood of damage. Thus, to the extent vacuum control is minimal in such embodiments, a "catch basket" is included to catch fragments of the cataract as the cutting element operates. To the extent pressure differential vacuum control is included in such embodiments to aid in the removal of macerated tissue and aid in stabilizing the cataract, the arrangement often results in inelegant communication between the screw, the aspiration system and any irrigation system, particularly if particles become stuck in the aspiration system.

The condition wherein a particle gets stuck, or "occludes", the aspiration during phacoemulsification can cause either sudden increases or drops in eye pressure, or significant fluid flow with concomitant turbulence inside the eye, which instances have great potential for intraocular damage. One such condition, referred to as post-occlusion surge (POS), is a well-known phenomenon in ocular surgery. During normal surgical conditions (i.e., when the phacoemulsification tip is not occluded), the vacuum level of the aspirator is relatively low. However, in a POS condition, occlusion at the emulsifying tip of the handpiece allows the aspirating vacuum to build (such as to a preset vacuum shutoff limit) until the blockage is broken. Upon breaking of the occlusion, stored energy in the tubing causes a rapid surge flow from the patient's eye, which can cause adverse effects to the structures within the eye. While mini-surges may happen hundreds of times during a typical phacoemulsification surgery, a major POS event may only happen occasionally, but with very significant adverse effects to the patient. By way of non-limiting example, the posterior capsule of the eye may be torn upon a POS.

For at least the foregoing reasons, there is a need for simpler and less expensive systems, apparatuses, and methods for performing cataract surgery. Such an apparatus, system and method would provide a surgical instrument for safe, controlled, and uncomplicated removal of a cataractous nucleus from the eye in its entirety, regardless of the maturity or hardness of the nucleus, while using a small eye incision size and with minimized risk of aspiration blockage-induced damage.

SUMMARY OF THE DISCLOSURE

The disclosure includes at least an apparatus, system and method for a handpiece for ocular surgical. The foregoing may include a handle having at least inlets for irrigation and aspiration; a sleeve extending distally from a first end of the handle, wherein the sleeve comprises a bore extending a length of the sleeve along a central axis of the sleeve, and comprises at least one port suitable to deliver the irrigation from the irrigation inlet substantially distally from the first end of the handle; the aspiration being provided at a bore port distal to the first end via fluidic communication between the aspiration inlet and the distal bore port; a motor coupled with a second end of the handle opposite the first end and having a motor shaft; and an auger associated with the motor shaft, and extending at least partially through an interior portion of the handle between the second end and the first end and extending along the length of the sleeve, wherein a tip of the auger distal to the motor shaft is advanced by actuation of the motor to emulsify an eye lens.

The apparatus, system and method may also include a handpiece for ocular surgery that provides interchangeable emulsification, which may include at least a hollowed handpiece body comprising a handle and a sleeve extending from the handle; irrigation and aspiration outputs at an operative end of the sleeve opposite the handle; and an interchangeable emulsifying assembly. The emulsifying assembly may include a motor; a motor mount suitable to receive the motor and interchangeably mount the motor to the handle opposite the sleeve; and an auger suitable for interchangeable operative connection to the motor, wherein the auger extends axially through the hollow and outwardly from the operative end.

Thus, the disclosure may provide simpler and less expensive systems, apparatuses, and methods for performing cataract surgery. The apparatus, system and method may provide a surgical instrument for safe, controlled, and uncomplicated removal of the cataractous nucleus from the eye in its entirety, regardless of the maturity or hardness of the nucleus, while using a small eye incision size and with minimized risk of aspiration blockage-induced damage.

BRIEF DESCRIPTION OF THE DRAWINGS

The accompanying drawings are included to provide a further understanding of the disclosure, and are incorporated into and thus constitute a part of this specification. The drawings illustrate disclosed embodiments and/or aspects and, together with the description, serve to explain the principles of the disclosure. In the drawings.

DETAILED DESCRIPTION

Figure 1:
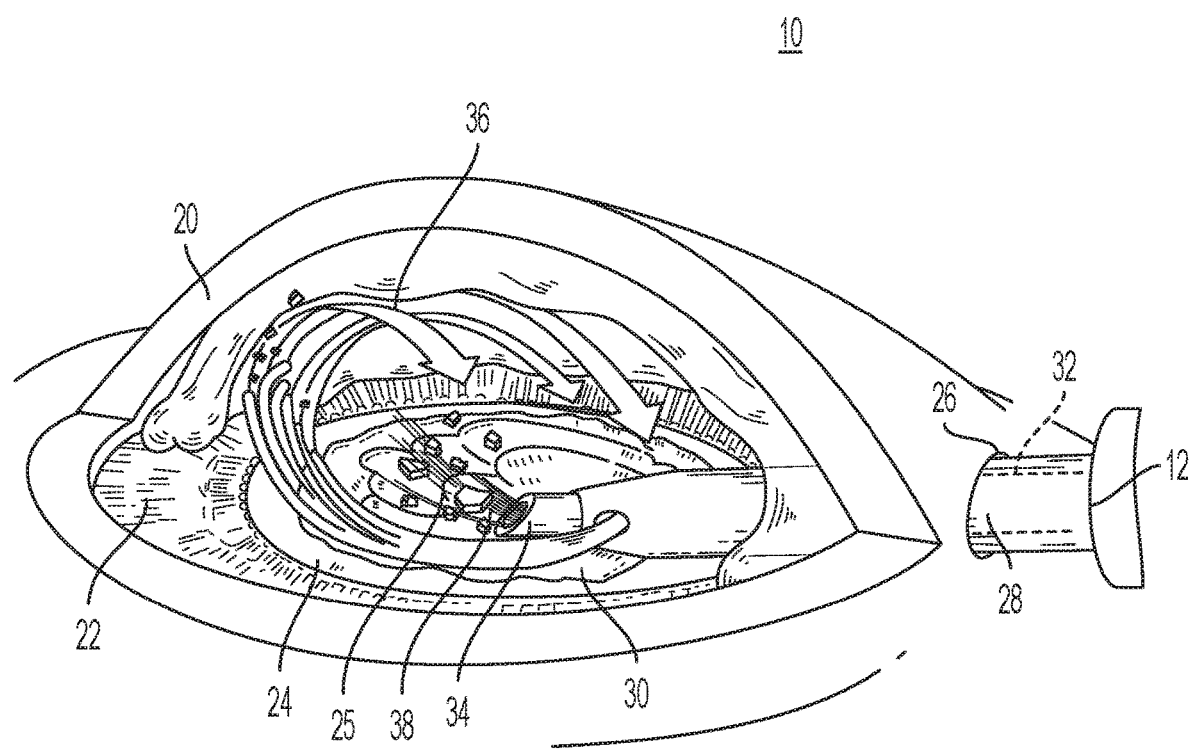
FIG. 1 is a cross-sectional view of an eye subjected to phacoemulsification surgery.

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical surgical, and particularly ophthalmic surgical, devices, systems, and methods. Those of ordinary skill may thus recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "upon", "connected to" or "coupled to" another element or layer, it may be directly on, upon, connected or coupled to the other element or layer, or intervening elements or layers may be present, unless clearly indicated otherwise. In contrast, when an element or layer is referred to as being "directly on," "directly upon", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements or aspects, these elements or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, component, region, layer or section discussed below could be termed a second element, component, region, layer or section without departing from the teachings of the disclosure.

Embodiments provide simpler and less expensive systems, apparatuses, and methods for performing cataract surgery. The apparatus, system and method provide a surgical instrument for safe, controlled, and uncomplicated removal of a cataractous nucleus from the eye in its entirety, regardless of the maturity or hardness of the nucleus, while using a small eye incision size and with minimized risk of aspiration blockage-induced damage.

With reference to FIG. 1, a cornea 20 of a human eye 10 is illustrated. The cornea 20 is a generally arcuate segment in front of the iris 22. The region between the iris and the cornea 20 is known as the anterior chamber of the eye. Directly behind the iris 22 is a lens capsule 24, and, in a healthy eye, a natural crystalline convex lens 25 is housed within the capsule 24 for focusing light, in cooperation with the cornea 20, upon the retina.

Through trauma, age or other causes, the natural crystalline lens 25 may become cloudy and fail to transmit and focus light in a proper manner. When this condition exists, a patient is said to have a "cataract," and the patient may become progressively functionally blind in the eye suffering from the cataract. Cataracts are a leading cause of blindness throughout the world, but a cataractous lens may be removed and replaced with an artificial intraocular lens to at least partially restore sight.

A currently preferred technique for removing a cataract lens is known as phacoemulsification, and this technique employs irrigation and aspiration in conjunction with ultrasound for emulsification of the affected lens 25. In phacoemulsification, an incision or opening 26 is surgically fashioned through the limbus portion of the eye. This opening serves to admit the tip of a phacoemulsification handpiece 12. The operative end 28 of the handpiece is operably extended through the cornea and into juxtaposition with lens 25.

In a conventional phacoemulsification, phacoemulsification handpiece, an electromagnetic core 32 internal to the handpiece 12 is ultrasonically excited from a power source. The core rapidly vibrates at between 10,000 and 100,000 cycles per second, for example. This rapid ultrasonic vibration serves to vibrate a tip 34 of the handpiece, which is brought into physical contact with the cataractous lens 25. The rapidly vibrating tip 34 physically emulsifies the cataract.

Concomitantly, an irrigation fluid 36 is supplied by the handpiece to commingle with and operably suspend bits of the emulsified cataract within, and further to maintain an acceptable pressure within, the anterior chamber. A vacuum 38 is also drawn by the handpiece, which serves to pull the irrigating fluid and suspended cataract material co-axially through the tip 34 and back to a collection reservoir.

In the embodiments of the present invention a phacoemulsification handpiece may employ a rotary motor and auger to perform emulsification of the eye lens, rather than employing the ultrasonic vibrating tip typically used to emulsify a cataractous lens in the known art. More specifically, in embodiments, the handpiece may include, passing substantially through a center axis thereof, an internal rotating rod acting as the emulsifying auger.

In embodiments, the internal auger may pass within an irrigating sleeve, wherein the irrigating sleeve may have one or more ports through which fluid may flow. For example, the auger may pass through a bore axially down the center of the irrigating sleeve, and the bore may also provide, such as therewithin or via a passageway through the auger, aspiration for removal of the lens emulsified by the auger. As such, embodiments may provide a handpiece, such as may include a handle having inputs/outputs to the sleeve ports and a sleeve having a center bore therethrough, formed of various materials, such as titanium or plastics.

The irrigation sleeve provided in the embodiments may not be subjected to ultrasonic vibration, as would be the case in the known art. Areas of the disclosed irrigation sleeve may be pre-shaped in something other than the known straight edged cylinder in the known art. For example, the sleeve may instead be pre-shaped to a variable thickness so to minimize wound leakage at the point of entry of the sleeve through the eye incision once the tip of the sleeve is within the subject eye.

Figure 2A:
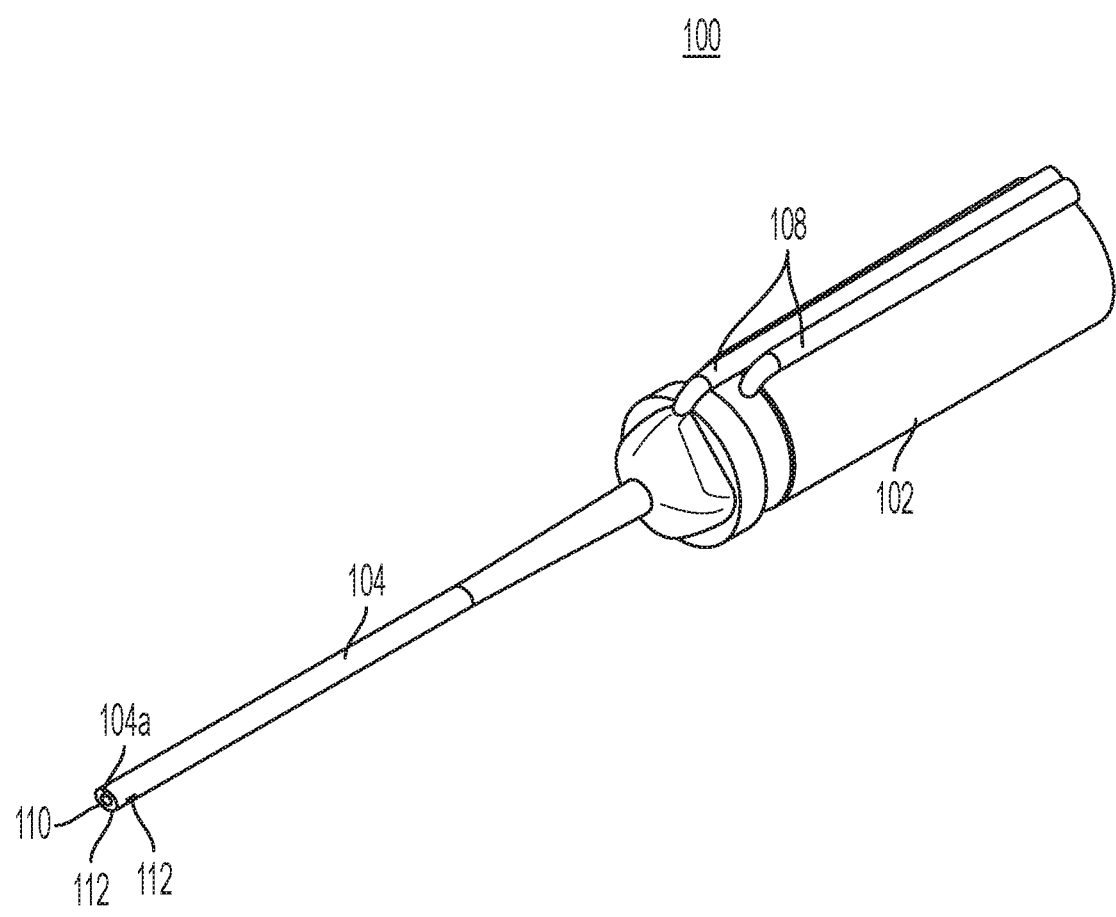
FIGS. 2A and 2B are illustrative views of an exemplary ocular surgical instrument.

As is illustrated in FIG. 2A, embodiments may include a handpiece 100 having a handle 102 physically associated with an outer sleeve 104. In the illustration, the hand piece 100 may be fixed, i.e., may be non-vibrating, thereby providing refined positional access to a cataractous lens. The hand piece 100 may include, such as passing through the handle thereof, one or more inlets and outlets 108, such as may be associated with the providing of irrigation to a port at or near the tip of the outer sleeve where the emulsification may occur, and/or aspiration to the tip of and/or otherwise from the bore 110 of the outer sleeve 104.

Figure 2B:
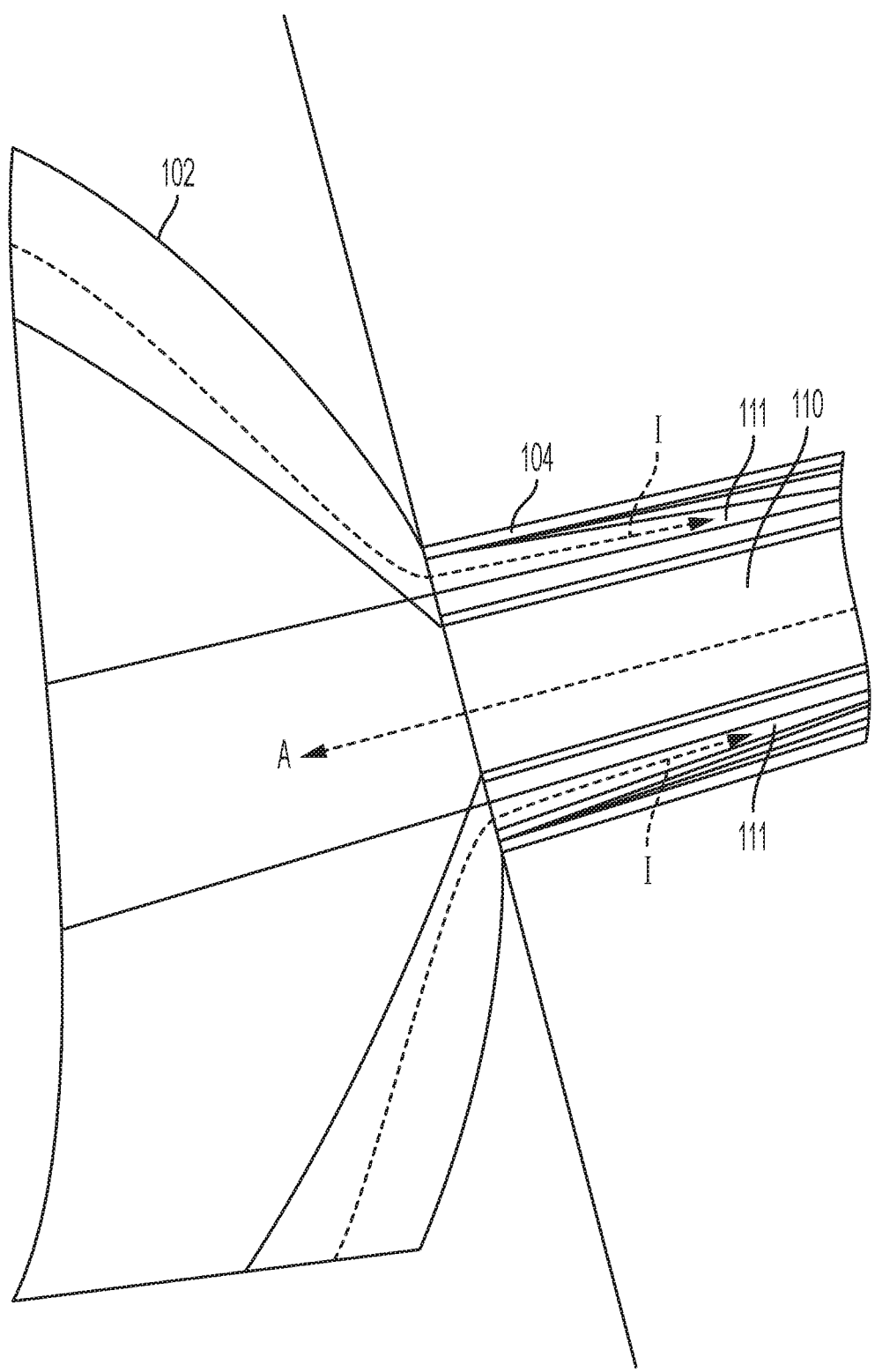

In the illustration, irrigation may outflow from one or more ports 112 on sleeve 104 as illustrated, such as via fluidic communication between ports 112 and the one or more inlets and outlets 108 shown as passing through the handle 102. Irrigation may flow along one or more paths, such as outer bore 111, outside of central bore 110, as shown in FIG. 2B. Other fluidics, such as including the aspiration for the cataractous lens, may also flow through or along the central bore 110 of the sleeve 104. Thereby, particles of the lens, such as including the cataract, may, during and after emulsification, be irrigated by the irrigation and aspirated via the center bore 110 of the outer sleeve 104. For example, maintenance of the requisite eye pressure for the emulsification may be enabled by irrigation that is provided via ports 112 in sleeve 104, while the aspiration port balances the irrigation fluid with the provided vacuum.

Figure 3:
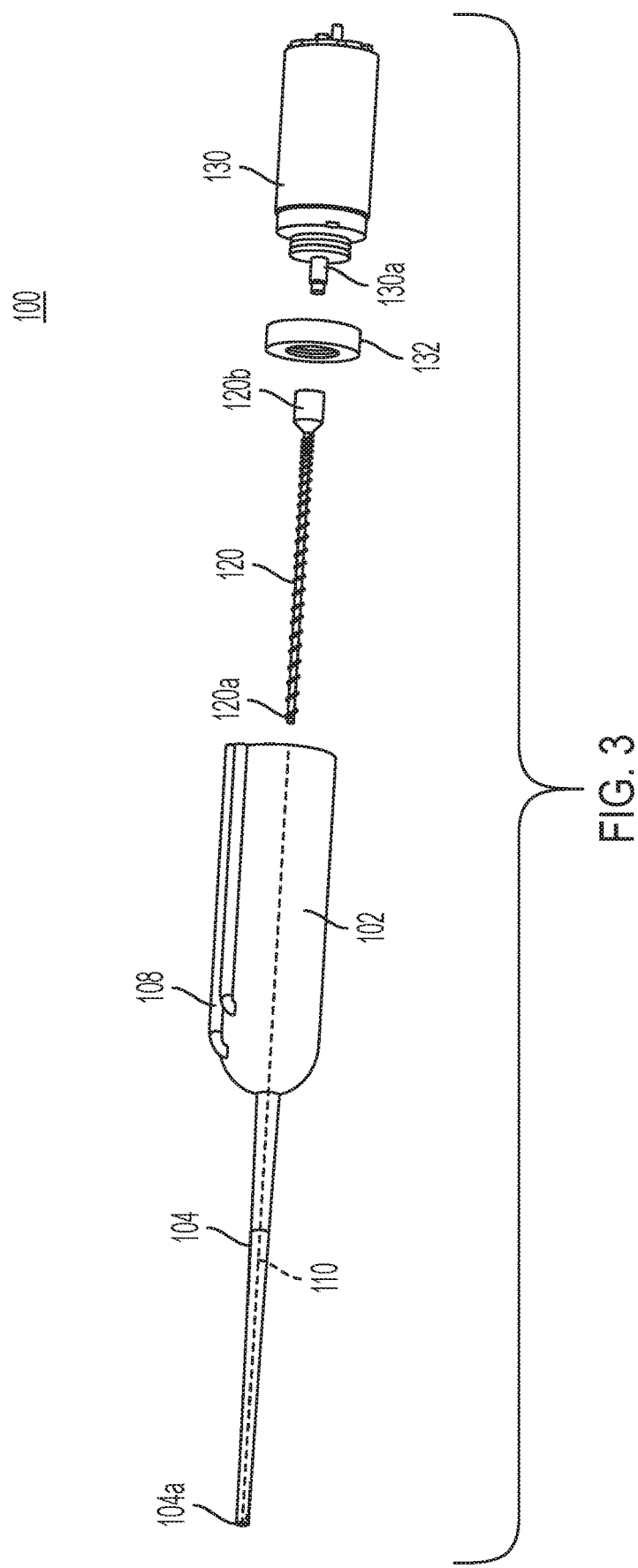
FIG. 3 is an illustrative view of an exemplary ocular surgical instrument.

With reference now also to FIG. 3 and in accordance with the foregoing, should an occlusion of the aspiration occur, such as because of a particle stuck at or near the tip 104a of the outer sleeve 104, the illustrated handpiece 100 may energize, or further energize, the rotating auger 120 passing through the center axis of the bore 110 of the outer sleeve 104. This energizing may be based on actuation of a rotary motor 130 operationally associated with a distal portion 120b of the auger 120, and may thereby fragment the occlusion. Accordingly, the occlusion may be continuously released by the rotation of the auger 120, rather than being suddenly sucked into clogging the aspirator as would be the case in the known art. As such, the disclosed solution better remedies the occlusion, as the removal of the occlusion may be dependent upon the rotation of the auger 120, rather than on the vibration of the handpiece tip and heightened use of the vacuum to remove the occlusion as would be the case in the known art. Of course, as will be understood to the skilled artisan in light of the discussion herein, a pitch of the auger 120 may be varied in order to best fragment the material of the cataractous lens to a preferred size, such as to thereby largely prevent occlusion of the aspiration line as compared to the known art.

The association of the outer sleeve 104, handle 102, and inlets and outlets 108 of FIG. 2 with an internal auger 120, an operating rotary motor 130, and mechanical link/protective o-ring 132 is illustrated, by way of example, in FIG. 3. More particularly, rotary motor 130 may be employed in order to rotate the auger 120 that passes through central bore 110 of the outer sleeve 104, as discussed throughout. The rotation of the auger 120 causes the auger to distally "advance" through the cataractous lens.

In an embodiment, outer sleeve 104 and/or a portion of handle 102 may be at least partially surrounded by a second outer sleeve (not shown). In this embodiment, outer sleeve 104 does not have the one or more ports 112, but rather the second outer sleeve may have one or more ports for the irrigation fluid to exit at the distal end of the second outer sleeve and have one or more corresponding fluid pathways along the central access of the outer sleeve 104 to direct the irrigation fluid out of the distal end. The second outer sleeve may be of any material known in the art, including a soft pliable polymer, e.g. silicone, or may be a metal material, e.g. titanium. The second outer sleeve may cover the distal end of outer sleeve 104 or at least a portion of the distal end of outer sleeve 104.

It is understood that the force required to bisect a cataractous lens varies with a number of factors, including the age of the patient, the extent of the cataract, the hardness of the lens, and various other factors. However, this force is generally in the range of about 0.25 to 2.25 Newtons of force, and may more particularly fall within a range of 0.5 to 1.7 Newtons of force, by way of non-limiting example. As this level of force would accordingly be required of the auger 120 in order to fragment the cataractus lens, the choice of motor 130 should be made in order to deliver the requisite force for a particular lens to be emulsified. As such, a motor 130 providing force to the auger 120 at the upper end of the aforementioned range(s) may work for all cataractous lenses, although such motors may be more expensive. Thus, various different motors 130 to rotate the referenced auger 120 may be selectable, such as based upon the power needed in accordance with the patient-centric factors discussed above.

Some embodiments may thus be modular, such as wherein various aspects, such as the outer sleeve 104 and/or the rotating auger 120 and/or the motor 130 may be variably and/or selectably associated with the handpiece, i.e., may be variably associated with the handle body 102. Thereby, aspects of the embodiments may provide interchangeable and/or disposable handpieces 100, either in part or in total. Further, variably autoclavable motors, based upon varying aspiration embodiments, may also be employed in the embodiments.

Further, the irrigation and aspiration inlets/outlets 108 and ports 112 may be located anywhere along the outer portion of the hand piece handle 102 and/or sleeve 104. This is because, at least in part, the outer sleeve 104 and handle 102 may merely provide a "shell" for the irrigation and aspiration fluidics supplied in conjunction with the auger 120. As will be understood in light of this shell functionality, the outer sleeve 104 may be built into and/or otherwise rigid in relation to the handle 102, at least because no vibration of the outer sleeve is necessary as it would be in the known art. Alternatively, sleeve 104 may be a wholly separate physical element from the handle 102.

More particularly, and as is evident from the example of FIG. 3, the lens material and/or fluid may flow from the distal end of sleeve 104 through the bore 110 to its respective inlet 108, and may thus be bounded by the auger 120 and the inner wall of the outer sleeve 104 or in another embodiment, a lumen created within the sleeve 104 may either surround the auger or run along the side of auger 120 within sleeve 104. Of note, the auger tip 120a may have a graduated pitch in order to ensure that particles are reduced to or below a certain size, such as to prevent occlusion of the aspiration via particles getting stuck between the inner wall of the bore opening 110 and the auger 120.

The opposing end 120b of the auger 120 may be operationally associated with a rotating motor shaft 130a of motor 130, as discussed throughout. The motor shaft 130a may, needless to say, thus serve to rotate the auger 120 at a rate correspondent to the force and speed of motor 130. The motor 130 may be physically associated with the handle 102 via a motor mounting 132, such as the o-ring assembly illustrated in FIG. 3.

The motor mounting 132 may be securely, detachably or non-detachably, physically associated with a hollowed distal portion of the handle 102, such as wherein the motor mount 132 and inner wall of the end of the handle 102 are mateably threaded, such that the motor 130 may be screwed into the handle 102 by mating of the motor mount threads to the receiving threads of the handle, and hence so that the auger 120 associated with the shaft 130a of motor 130 passes through the bore 110 axially through the outer sleeve 104. A plastic or rubberized o-ring may or may not be associated with an o-ring groove of the motor mount 132, such that the motor 130, motor shaft 130a and auger 120 may be sealed to the hand piece 120 in order to avoid fluidic leakage from the handpiece 100.

As discussed throughout, any of a variety of motors 130 sufficient to provide the requisite force for a given cataractous lens may be employed in the embodiments. The selected motor 130 should provide sufficient torque so as to turn the auger 120 at an acceptable rate when pulling cataract material into the proximal tip 104a of the outer sleeve 104. Accordingly, a motor 130 of any size to provide the requisite torque may be employed in the embodiments, although certain motors, such as an 8 mm diameter by 22 mm long motor, may result in shorter and thinner handpieces 100 for phacoemulsification than are provided in the known art.

Figure 4:
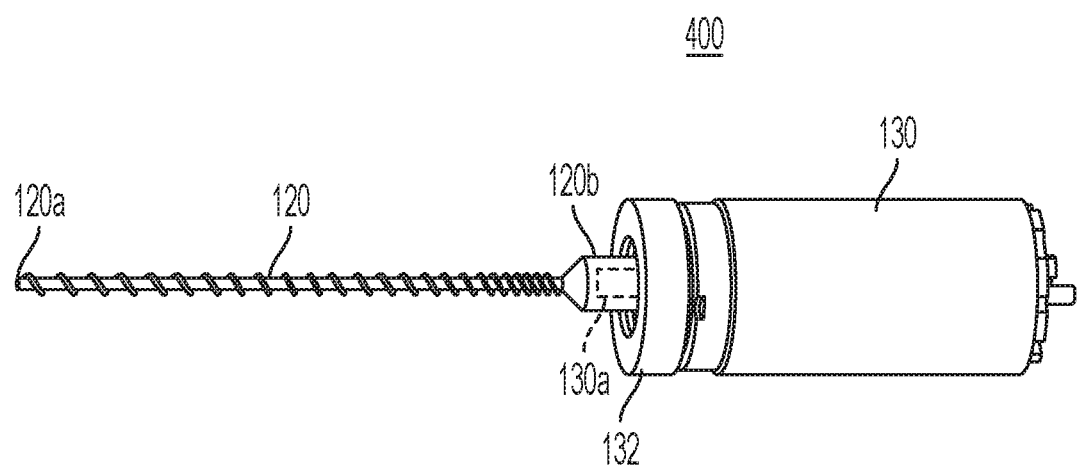
FIG. 4 is an illustrative view of an exemplary ocular surgical instrument.

A motor 130 and auger 120 assembly 400 is illustrated in the embodiment of FIG. 4. In the illustration, it will be understood that the auger 120 may be detachably associated with the motor shaft 130a, or may be permanently affixed to the motor shaft 130a. Further, it will be understood that the auger 120, o-ring/mounting assembly 132, and/or motor 130 may be used disposably or nondisposably, such as based upon the use-case. Moreover, it will be appreciated, to the extent augers 120 are changeably associated with motors 130, that any of a variety of augers 120, and/or any of a variety of motors 130, may be variably employed in phacoemulsification, such as based on patient characteristics and/or characteristics of the cataractous lens, by way of non-limiting example.

It will be appreciated that a combination phacoemulsification and irrigation/aspiration hand piece 100 may be provided in the embodiments. Additional and alternative aspects to those discussed throughout may also be provided. Of note, an insert (not shown) may be provided to extend beyond the external portion of the outer sleeve. This insert may have soft silicon protrusions, for example, which may be used to engage in a manual scrub. Additionally, the insert may interlock with the auger discussed throughout, such as via any known methodology, to thereby use the disclosed hand piece to spin the silicon protrusions.

Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to be included within the scope of the disclosure.

What is claimed is:

1. A handpiece for ocular surgery, comprising:
   a handle having an irrigation inlet and an aspiration inlet;
   a sleeve extending distally from a first end of the handle and culminating in an operative end, wherein the sleeve comprises a bore extending a length of the sleeve along a central axis of the sleeve, and comprises at least one port suitable to deliver irrigation from the irrigation inlet substantially distally from the first end of the handle;
   aspiration being provided at a bore port distal to the first end via fluidic communication between the aspiration inlet and the bore port;
   a motor coupled with a second end of the handle opposite the first end and having a motor shaft; and
   an auger associated with the motor shaft and extending at least partially through an interior portion of the handle between the second end and the first end and extending along the central axis of the sleeve, wherein a tip of the auger extends beyond the operative end of the sleeve and is configured to rotate upon actuation of the motor to thereby emulsify an eye lens, wherein the auger comprises a graduated pitch that increases in a direction from the motor shaft to the tip of the auger and is operable to fragment material of the eye lens to a preferred size.

2. The handpiece of claim 1, wherein the sleeve is non-vibrating.

3. The handpiece of claim 1, wherein the actuation of the motor is variable.

4. The handpiece of claim 3, wherein the variable actuation is dependent upon a level of occlusion of the aspiration.

5. The handpiece of claim 1, wherein the motor is detachably affixed to the handle.

6. The handpiece of claim 5, wherein the motor is detachably affixed to the handle using a motor mount.

7. The handpiece of claim 6, wherein the motor mount comprises threads on the second end of the handle.

8. The handpiece of claim 6, further comprising mateable threading between the motor and the second end of the handle.

9. The handpiece of claim 6, wherein the motor mount comprises a sealing o-ring.

10. The handpiece of claim 9, wherein the sealing o-ring comprises rubber.

11. The handpiece of claim 1, wherein the motor is suitable to deliver a force in a range of about 0.25 to 2.25 Newtons to the tip.

12. The handpiece of claim 1, wherein the auger is detachably associated with the motor shaft.

13. A handpiece for ocular surgery providing interchangeable emulsification, comprising:
    a hollowed handpiece body comprising a handle and a sleeve extending from the handle;
    irrigation and aspiration outputs at an operative end of the sleeve opposite the handle;
    an interchangeable emulsifying assembly, comprising:
      a motor;
      a motor mount suitable to receive the motor and interchangeably mount the motor to the handle opposite the sleeve; and
      an auger suitable for interchangeable operative connection to the motor, wherein the auger extends axially through the hollowed handpiece body and outwardly from the operative end of the sleeve, wherein the auger comprises a graduated pitch that increases in a direction from the motor to the operative end of the sleeve, wherein the graduated pitch is operable to fragment material of an eye lens to a preferred size.

14. The handpiece of claim 13, wherein the auger is one of a plurality of augers each suitable for interchangeable operative connection to the motor, and wherein each of the plurality of augers comprise different pitches, and wherein the pitches correspond to characteristics of different cataracts.

15. The handpiece of claim 13, wherein the motor is one of a plurality of motors suitable for interchangeable operative connection to the motor mount and to the auger, wherein each of the plurality of motors is configured to produce a different motor power, and wherein the motor powers correspond to characteristics of different cataracts.

16. The handpiece of claim 13, further comprising mateable threading between the motor amount and the handle.

17. The handpiece of claim 13, wherein the motor mount comprises a sealing o-ring.

18. The handpiece of claim 17, wherein the sealing o-ring comprises plastic.

19. The handpiece of claim 13, wherein the motor is suitable to deliver a force in a range of about 0.25 to about 2.25 Newtons to the auger.

* * * * *